United States Patent
McNair

(10) Patent No.: US 11,062,802 B1
(45) Date of Patent: Jul. 13, 2021

(54) MEDICAL RESOURCE FORECASTING

(71) Applicant: Cerner Innovation, Inc., Kansas City, KS (US)

(72) Inventor: Douglas S. McNair, Leawood, KS (US)

(73) Assignee: CERNER INNOVATION, INC., Kansas City, KS (US)

(*) Notice: Subject to any disclaimer, the term of this patent is extended or adjusted under 35 U.S.C. 154(b) by 807 days.

(21) Appl. No.: 15/173,063

(22) Filed: Jun. 3, 2016

Related U.S. Application Data

(60) Provisional application No. 62/170,696, filed on Jun. 4, 2015.

(51) Int. Cl.
*G16H 40/20* (2018.01)
*G16H 50/30* (2018.01)

(52) U.S. Cl.
CPC ............. *G16H 40/20* (2018.01); *G16H 50/30* (2018.01)

(58) Field of Classification Search
CPC .............................. G16H 40/20; G16H 50/30
USPC ......................................................... 705/2
See application file for complete search history.

(56) References Cited

U.S. PATENT DOCUMENTS

| | | | |
|---|---|---|---|
| 6,205,431 B1 * | 3/2001 | Willemain | G06Q 10/04 705/7.25 |
| 7,587,329 B2 | 9/2009 | Thompson et al. | |
| 8,234,149 B2 | 7/2012 | Spearman | |
| 8,799,009 B2 | 8/2014 | Mellin et al. | |

(Continued)

FOREIGN PATENT DOCUMENTS

| | | | |
|---|---|---|---|
| CN | 101782763 A | * 7/2010 | |
| WO | WO-0077665 A2 | * 12/2000 | ............ G06Q 10/06 |

OTHER PUBLICATIONS

Marlena Silva Marchena, Measuring and implementing the bullwhip effect under a generalized demand process, Oct. 19, 2010, Cornell University https://arxiv.org/abs/1009.3977, pp. 6-7, 17-20 (Year: 2010).*

(Continued)

*Primary Examiner* — Robert A Sorey
*Assistant Examiner* — Kimberly A. Sass
(74) *Attorney, Agent, or Firm* — Shook, Hardy & Bacon L.L.P.

(57) ABSTRACT

Systems, methods and computer-readable media are provided for determining appropriate staffing levels above acuity-based forecast baseline values, to provide compliance with regulatory 'patient-to-nurse' ratio thresholds within a given service level or statistical probability. A non-zero and optionally stochastically varying leadtime may be provided for sourcing nurses and may ascertain whether significant patient demand and labor supply chain interdependencies exist via the bullwhip ratio, using predictive modeling based on a 'safety-stock-over-leadtime' (SSL). Variations that may arise according to different healthcare institutions' policies for shift-bidding, scheduling, use of contract nursing resources, and other aspects, may be accounted for in the predictive models. Further, some embodiments include providing decision support recommendations for adjusting health services staff to evolving patient needs in near real-time, and may further include automatically scheduling these employees and/or notifying them of work schedule changes.

15 Claims, 7 Drawing Sheets

(56) References Cited

U.S. PATENT DOCUMENTS

| | | |
|---|---|---|
| 10,249,385 B1 | 4/2019 | McNair et al. |
| 10,417,379 B2 | 9/2019 | Tanner, Jr. et al. |
| 2002/0174005 A1 | 11/2002 | Chappel |
| 2005/0032066 A1 | 2/2005 | Heng et al. |
| 2006/0177041 A1 | 8/2006 | Warner et al. |
| 2009/0319292 A1 | 12/2009 | Warner et al. |
| 2010/0198609 A1 | 8/2010 | Mellin et al. |
| 2010/0262452 A1* | 10/2010 | Gibson .......... G06Q 10/063112 705/7.14 |
| 2014/0013658 A1 | 1/2014 | Silverman et al. |
| 2014/0136458 A1 | 5/2014 | Levin et al. |
| 2015/0254370 A1 | 9/2015 | Sexton et al. |
| 2017/0024523 A1 | 1/2017 | Gutfraind et al. |

OTHER PUBLICATIONS

R. D. Snyder, A.B. Koheler and J.K. Ord, Lead Time Demand for Simple Exponential Smoothing: An Adjustment Factor for the Standard Deviation, Oct. 1999, The Journal of the Operational Research Society, vol. 50, No. 10, p. 1081 (Year: 1999).*

Non-Final Office Action received for U.S. Appl. No. 15/785,147, dated Oct. 2, 2019, 18 pages.

Final Office Action received for U.S. Appl. No. 15/785,147, dated Mar. 16, 2020, 21 pages.

Non-Final Office Action received for U.S. Appl. No. 15/785,147, dated Mar. 23, 2021, 10 pages.

* cited by examiner

|  | TRADITIONAL STAFFING N(PATIENTS) = 1,651 N(BEDS) = 24 | SSL STAFFING (95% SERVICE LEVEL) N(PATIENTS) = 2,226 N(BEDS) = 24 | P-LEVEL |
| --- | --- | --- | --- |
| DESCRIPTION OF STAFF (PER SHIFT) | | | |
| MEAN PATIENT-TO-NURSE RATIO (SD) | 1.58 (0.30) | 1.46 (0.27) | 0.04 |
| MEAN NURSES (SD) | 11.41 (2.00) | 12.37 (2.12) | 0.29 |
| PERCENT SHIFTS WITH P/N > 2.0 | 10.1% | 2.0% | <0.001 |
| DESCRIPTION OF WORKLOAD (PER SHIFT) | | | |
| MEAN PATIENT TURNOVER (SD) | 5.2 (6.8) | 5.0 (6.6) | 0.83 |
| DESCRIPTION OF PATIENTS (PER SHIFT) | | | |
| MEAN NUMBER OF PATIENTS (SD) | 18.10 (4.57) | 18.3 (4.64) | 0.76 |
| PROPORTION OF MEN (SD) | 0.63 | 0.60 | 0.35 |
| MEAN AGE (SD) | 61.3 (3.7) | 61.5 (4.0) | 0.41 |
| BULLWHIP EFFECT | | | |
| MEAN BULLWHIP RATIO (SD) | 1.55* (0.27) | 1.42* (0.24) | <0.001 |

* SIGNIFICANTLY DIFFERENT FROM 1.0, P <0.0001

*FIG. 4.*

```
###########################################################

# CERDSM - SSL nurse staffing ICU

##################################################### library(forecast)
library(SCperf)

# load 100 shifts data
demand <- as.ts(read.csv(file="c:/0_cerdsm/IP/capacity/sslt/demand.csv", header=TRUE,
colClasses="numeric"))

# initialize params
L <- 1      # L positive lead-time [1,inf)
p <- 2      # order to be used in the SMA method
a <- 0.7    # alpha smoothing factor to be used in the ES method (0 < alpha < 1)
SL <- 0.54
phi <- rep(0,70)
fc <- rep(0,70)
fc_ssl <- rep(0,70)
bw <- rep(0,70)

# perform ES SSL calculations for timeseries with moving 30-shift window with 95% service level
for (i in 1:70){
  fit <- Arima(demand[i:(29+i)], order=c(1,0,0), transform.pars=TRUE, include.drift=TRUE)
  fc[i] <- round(as.numeric(forecast(fit, h=1)$mean),2)
  phi[i] <- fit$model$phi[1]
  ssl_e <- SSL("ES", phi[i], L, p, a, SL)
  fc_ssl[i] <- round(fc[i]*(1 + ssl_e), 0)
  bw[i] <- bullwhip("ES", phi[i], L, p, a)
} write.csv(fc, file="c:/0_cerdsm/IP/capacity/sslt/fc1.csv")
write.csv(phi, file="c:/0_cerdsm/IP/capacity/sslt/phi1.csv")
write.csv(fc_ssl, file="c:/0_cerdsm/IP/capacity/sslt/fc_ssl1.csv")
write.csv(bw, file="c:/0_cerdsm/IP/capacity/sslt/bw1.csv")
```

*FIG. 6.*

MEDICAL RESOURCE FORECASTING

CROSS-REFERENCE TO RELATED APPLICATIONS

This application claims the benefit of U.S. Provisional Application No. 62/170,696, entitled "Staffing Resource Forecasting," filed on Jun. 4, 2015, which is incorporated by reference in its entirety.

BACKGROUND

Aligning nursing resources with patients' needs is important to safety, particularly in critical care. An increasing number of studies demonstrate that patient-to-nurse (P/N) ratios greater than 2.00 in critical care units are associated with increased mortality and increased incidence of failure to rescue. Additionally, California 22 CCR § 70217(a)(1) and similar regulations in other jurisdictions have for many years required that the nurse-to-patient ratio in critical care units shall be 1:2 or less at all times. A recently-enacted Massachusetts regulation 958 CMR 8.04(2) states that the maximum for each staff nurse may not exceed two ICU patients at any time during a shift. Compliance with rules such as these places extraordinary priority on planning shift staffing so as to remain under a P/N ratio of 2.00 a much higher percentage of the time than presently occurs.

However, workload within an ICU fluctuates dramatically, both shift-to-shift and within-shift. Shift-wise patient turnover is high, sometimes exceeding 50% depending on the type of ICU, and it is highly variable shift-to-shift. The number of life-sustaining procedures that are required on an unpredictable urgent-emergent basis is high and is also widely varying. For these reasons, even modern acuity measurement software and decision-support systems have difficulty estimating the staffing that will be required on a critical care unit within a time horizon of one or two shifts.

SUMMARY

Systems, methods and computer-readable media are provided for reliably determining appropriate staffing levels above acuity-based forecast baseline values, to provide compliance with regulatory 'patient-to-nurse' ratio thresholds within a given service level or statistical probability. In particular, embodiments of the invention may provide for non-zero and optionally stochastically varying leadtime for sourcing nurses and may ascertain whether significant patient demand and labor supply chain interdependencies exist via the bullwhip ratio. By determining that a significant bullwhip effect is present in ICU nurse staffing, predictive modeling of 'safety-stock-over-leadtime' (SSL) may be used to achieve improvements in units' meeting their Patient to Nurse (P/N) targets as established by current regulations for nurse staffing in critical care. Some embodiments also accommodate variations likely to arise according to different healthcare institutions' policies for shift-bidding, scheduling, use of contract nursing resources, and other aspects, which may be reflected as variations in the bullwhip ratio. Further, some embodiments of the invention support recommendations for adjusting nursing (or health services employee staff) resources to evolving patient needs in near real-time, and may include automatically scheduling these employees and/or notifying them of work schedule changes. In this way, embodiments of the invention enable reliable estimation of safety-stock-over-leadtime (SSL) for nurse staffing or other labor resource constrains production or service delivery. Moreover, in addition to benefits of regulatory compliance and likely benefits in terms of improved survival and failure-to-rescue rates, it is possible that nurse staffing based on acuity and SSL forecasting may help to reduce stress, improve nurses' quality of life, or improve retention in the profession.

BRIEF DESCRIPTION OF THE DRAWINGS

The present invention is described in detail below with reference to the attached drawing figures, wherein:

FIG. 4 depicts a table comparing traditional staffing vs. SSL staffing, in accordance with an embodiment of the invention;

FIG. 6 illustratively provides an example embodiment of a computer program routine used for forecasting staffing with SSL, in accordance with an embodiment of the invention.

DETAILED DESCRIPTION

Figure 1A:
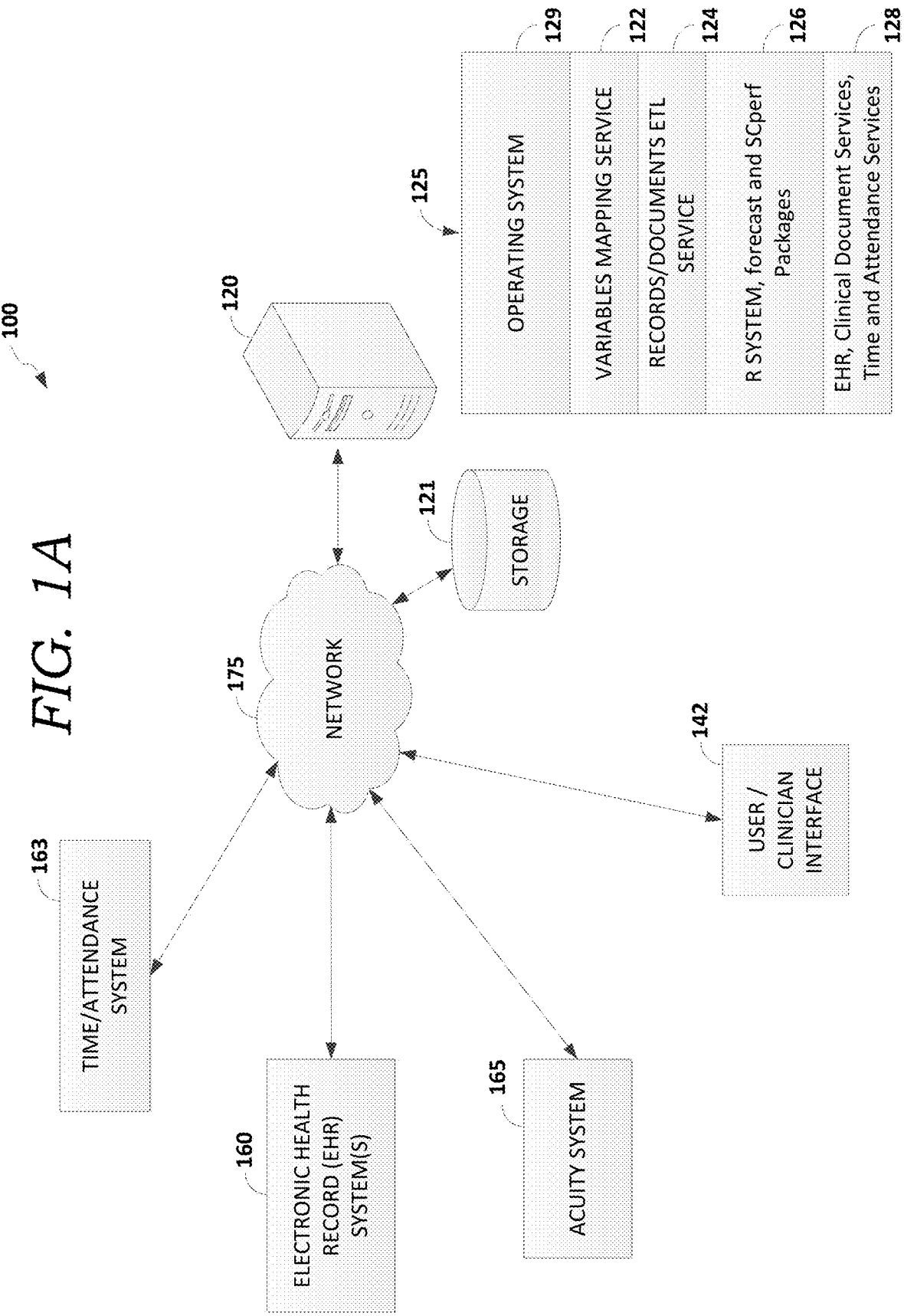
FIGS. 1A and 1B depict aspects of an illustrative operating environment suitable for practicing an embodiment of the invention.

The subject matter of the present invention is described with specificity herein to meet statutory requirements. However, the description itself is not intended to limit the scope of this patent. Rather, it is contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In an embodiment, the invention takes the form of a computer-program product that includes computer-usable instructions embodied on one or more computer readable media.

Computer-readable media can be any available media that can be accessed by a computing device and includes both volatile and nonvolatile media, removable and non-removable media. By way of example, and not limitation, computer-readable media comprises media implemented in any method or technology for storing information, including computer-storage media and communications media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 100. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Accordingly, at a high level, this disclosure describes, among other things, methods and systems, for determining appropriate staffing levels for health care services. Staffing levels may be determined that are above acuity-based forecast baseline values, for compliance with regulatory 'patient-to-nurse' ratio thresholds within a given service level or statistical probability. In particular, embodiments of the invention may provide for non-zero and optionally stochastically varying leadtime for sourcing nurses and may ascertain whether significant patient demand and labor supply chain interdependencies exist via the bullwhip ratio. By determining that a significant bullwhip effect is present in ICU nurse staffing, predictive modeling of 'safety-stock-over-leadtime' (SSL) may be used to achieve improvements in units' meeting their P/N targets as established by current regulations for nurse staffing in critical care. In this way, embodiments of the invention enable reliable estimation of safety-stock-over-leadtime (SSL) for nurse staffing or other labor resource constrains production or service delivery.

In balancing competing priorities, it is important that nursing staffing provide enough nurses to safely and effectively care for the patients. Historical solutions for nurse staffing requirements forecasting have several shortcomings, including: (1) Failing to determine the patient-arrival, -care, and -departure processes; (2) Inadequately accounting for sources of variability in workload, such as patient acuity and turnover; (3) Failure to determine the nurse sourcing processes; (4) Assuming instantaneous sourcing of nurses to work a shift (infinite capacity; leadtime=0); (5) Assuming supply and demand processes are constant/unchanging; (6) Failing to take into account finite bed capacity of nursing unit (saturation); (7) Failing to account for dependencies between supply and demand; and (8) Heteroskedasticity of variances of supply and demand processes. These shortcomings result in a high prevalence of statistically inaccurate forecasts, such that excesses and shortages occur frequently. Accordingly, it is therefore highly valuable and highly desirable to provide embodiments of the methods and systems described herein for ameliorating these limitations and providing superior accuracy in staffing to comply with applicable regulatory thresholds and safety guidelines, and to do so in a cost-effective, sustainable manner.

Although mathematical models to predict optimal 'safety stocks' are used in supply chain management, such models previously have not been effectively applied to workforce management because of the differences between the two disciplines. Nevertheless various aspects may exhibit similarities, such as evolving demand forecast according to acuity and the fact that provisioning 'stock' to meet demand in a future period has non-zero variable lead-time. Under certain assumptions about the forecasts (for example, the demand process is well-fit as an autoregressive process) and about the labor supply process (e.g., one or more shifts' lead-time are needed for engaging personnel to work the shift), some embodiments of the invention may establish that safety stock over lead-time (SSL) for such systems is effectively equivalent to the corresponding problem for systems with stationary demand bounds and base stock policies. Models resembling those utilized in supply chain analytics therefore may be effective for determining the optimal safety levels of nurse staffing. In this way, embodiments of the invention may lead to significant benefits from the inclusion of the forecast process when determining the optimal safety stocks in health care services.

In some embodiments, a health services staff laborer on a shift, such as nurse on a shift in ICU nurse staffing, may be abstractly modeled as a 'resource' in 'inventory' and each patient is modeled as a source of 'demand'. In this example, it may be assumes that the processes that govern the patient arrivals and departures from an ICU ('demand process') and the provisioning of nursing resources in that ICU ('response process') are, like supply chain problems, amenable to accurate mathematical modeling so long as the amount or length of the data available is sufficient to capture the characteristic features of those processes, including shift-of-day, day-of-week and possibly also seasonal effects. In particular, one embodiment incorporates modeling of non-zero leadtime for contacting and engaging additional nurses to work a shift on which increased census and/or acuity is forecast.

In the context of manufacturing operations, the magnification of variations in demand as one moves up a supply chain is reminiscent of a cracking whip, and has been termed the 'bullwhip effect.' This effect may be measured by a parameter such as a ratio involving the unconditional variance of the response process in the numerator and the unconditional variance of the demand process in the denominator. Such a ratio may be termed a "bullwhip ratio." In an embodiment variance is estimated by a sample variance, subject to a lower limit for minimum variance. In an embodiment an estimated variance is added to a minimum value to form a rubust estimator, and to avoid problems related to a near division by zero condition. In an embodiment the variance is estimated by a sample absolute difference. If the estimated bullwhip ratio is equal to one there is no variance magnification, while a ratio greater than one means that the bullwhip effect is present. On the other hand, bullwhip ratio less than one means that the response process is being smoothed over time compared to fluctuations in the demand.

Five chief causes of the bullwhip effect are known in manufacturing supply chains: inaccuracies in demand forecasting, supply shortages, non-zero lead times, batch ordering, and price variations. A number of approaches may be implemented for reducing the impact of the bullwhip effect. For instance, one approach is the centralization of demand information—that is, providing each stage of the supply chain with complete information regarding demand so that managers can implement optimal smoothing of the response in terms of resources in the supply chain.

The current 'big data' era facilitates mathematical and machine-learning based approaches to improving the accuracy, resilience, and agility of quantitative optimization of staffing forecasting in healthcare. Mathematical model-driven balancing of acuity-based workload and staffing resources via SSL modeling promises to enable compliance with safety-motivated P/N threshold standards in an efficient, cost-effective manner In some embodiments, such models may automatically and dynamically adapt to evolving casemix, census, and acuity levels, as well as evolving staff sourcing in each unit. Additionally, efficiency of provisioning nursing resources may be further improved by implementing or modifying policies and procedures for reducing bullwhip-type impacts on nurse staffing, in ICUs and perhaps in other unit types as well. Accordingly, embodiments of the invention may determine that a bullwhip effect is present in ICU nurse staffing and use predictive modeling of 'safety-stock-over-leadtime' (SSL) to achieve improvements in units' meeting their P/N targets as established by current regulations for nurse staffing in critical care.

Referring now to the drawings in general, and initially to FIG. 1A in particular, an aspect of an operating environment 100 is provided suitable for practicing an embodiment of our invention. We show certain items in block-diagram form more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1, example operating environment 100 provides an aspect of a computerized system for compiling and/or running aspects of the invention including predicting appropriate staffing levels for health care services for compliance with regulatory 'patient-to-nurse' ratio thresholds within a given service level or statistical probability. Environment 100 includes one or more electronic health record (EHR) systems, such as hospital EHR system 160, communicatively coupled to network 175, which is communicatively coupled to computer system 120. In some embodiments, components of environment 100 that are shown as distinct components may be embodied as part of or within other components of environment 100. For example, EHR systems 160 may comprise one or a plurality of EHR systems such as hospital EHR systems, health information exchange EHR systems, ambulatory clinic EHR systems, psychiatry/neurology EHR systems, and may be implemented in computer system 120. Similarly, EHR system 160 may perform functions for two or more of other EHR systems (not shown). In an embodiment EHR system 160 is comprised of one or more client computing devices, such as a workstation, a desktop, personal computer, a laptop, a smartphone, or a tablet computing device.

Network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) system 160 include one or more data stores of health records, which may be stored on storage 121, and may further include one or more computers or servers that facilitate the storing and retrieval of the health records. In some embodiments, EHR system 160 may be implemented as a cloud-based platform or may be distributed across multiple physical locations. EHR system 160 may further include record systems, which store real-time or near real-time patient (or user) information, such as a computer system and/or a wearable, bedside, or in-home patient monitors, for example.

Example operating environment 100 further includes provider user/clinician interface 142 communicatively coupled through network 175 to an EHR system 160, patient acuity system 165, and employee time/attendance system 163. Although environment 100 depicts an indirect communicative coupling between interface 142 and EHR system 160 through network 175, it is contemplated that an embodiment of interface 142 is communicatively coupled to EHR system 160 directly. An embodiment of interface 142 takes the form of a user interface operated by a software application or set of applications on a client computing device such as a personal computer, laptop, smartphone, or tablet computing device. In an embodiment, the application includes the PowerChart® software manufactured by Cerner Corporation. In an embodiment, the application is a Web-based application or applet. A provider, manager, or clinician application facilitates accessing and receiving information from a user or health care provider about a specific patient or set of patients, or health care worker or set of health care workers. Embodiments of interface 142 also facilitates accessing and receiving information from a user or health care provider about a specific patient or population of patients (including patient history), healthcare worker; health care resource data; variables measurements, time series, and predictions (including plotting or displaying the determined outcome and/or issuing an alert) described herein; or other health-related information, and facilitates the display of results, recommendations, or orders, for example. In an embodiment, interface 142 also facilitates receiving orders for the patient from the clinician/user, scheduling healthcare resources or staffing, based on the results of monitoring and predictions. Interface 142 may also be used for providing diagnostic services or evaluation of the performance of various embodiments.

One embodiment of user/clinician interface 142 takes the form of a user interface and application, which may be embodied as a software application operating on one or more mobile computing devices, tablets, smartphones, front-end terminals in communication with back-end computing systems, laptops, or other computing devices. In an embodiment, interface 142 includes a Web-based application or set of applications usable to manage user services provided by an embodiment of the invention. For example, in an embodiment, manager 140 facilitates processing, interpreting, accessing, storing, retrieving, and communicating information acquired from EHR 160, or storage 121, including employee staffing related information. In an embodiment, interface 142 sends a notification (such as an alarm or other indication) directly to user/clinician or other manager through network 175. In one embodiment, interface 142 may automatically schedule staffing at a future time period, and may also notify employees (such as nurses) based on forecasted levels determined in accordance with an embodiment of the invention. As shown in example environment 100, in one embodiment, interface 142 is communicatively coupled to patient acuity system 165 and employee time/attendance system 163, through network 175.

Example operating environment 100 further includes computer system 120, which may take the form of a server, which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, a portion of computing system 120 may be embodied on user/clinician interface 142. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

In an embodiment a user interface 142 presents an information display and a graphical user interface for a nursing administrator at a first location, e.g. a mobile location. The user interface 142 is enabled by a tablet computer running a staffing applet that runs as a time and attendance service 128 on operating system 129. Such a tablet computer is, for example, assigned to a nursing administrator for staffing supervision of an acute care unit, and manages a staffing notification system that sends out alerts by text message or email to notify each staff member selected that he or she is needed on an upcoming shift.

In an embodiment, the user interface 142 presents information such as a menu of compute times for staffing needed for the next shift, e.g. 1 hour, 2 hours, 3 hours, or 4 hours prior to the next shift. In an embodiment a selected compute time for staffing determines a fixed constant lead-time for all shifts, and stores this predetermined lead-time in storage 121. In an embodiment, the user interface 142 presents one or more options such as menu prompts enabling an administrator to select one or more of a lead-time "auto-compute" option, a number of shifts per day, and a partitioning option. An auto-compute option, when selected, instructs the staffing service to compute the staffing needs for the upcoming shift at a time that allows an estimated lead-time to expire after needed staff members are notified. For example, if lead-time estimation determines that a lead-time of 47 minutes is needed for an upcoming shift, then the system automatically begins computing staffing level 48 minutes prior to a shift change, thus allowing one minute for the system to perform the computation and to deliver staffing notification messages. In an embodiment, the estimation of lead-time is performed within a lead-time estimation component that runs as a time and attendance service in 128. In an embodiment, the lead time is estimated using a linear estimate that forms a weighted linear combination of lead-times needed in several prior instances. In an embodiment weights are chosen to give more statistical weight to recent samples, and relatively less weight to samples more distant in the past. In an embodiment the weights are chosen from an exponential decay of a chosen parameter over a moving window of recent samples. In an embodiment lead-time is computed once per shift. In an embodiment lead-time is computed more than once per shift, such as every hour. In an embodiment, when the estimated lead-time is within a guard interval (e.g. one half-hour) of the time remaining in a shift, the staffing requirements are computed with best available data.

A number of shifts per day may present a number field accepting, for example, 2, which is then mapped to a schedule of 12 hour shifts; or 3, which is in turn mapped to a schedule of three eight hour shifts, etc. A partitioning option (yes or no) when selected partitions one or more data sets so that like shifts are grouped together for estimation purposes. For example, with a 3 shift option, when the partitioning selection is active the partition of day-shifts are grouped together for parameter estimation, the partition of evening shifts are grouped together for parameter estimation, and the partition of night-shifts are grouped together for parameter estimation. In an embodiment a parameter is lead-time and/or shift modeling parameters such as weights, auto-regressive parameters, moving average parameters, decay parameters, etc.

In an embodiment, the user interface 142 presents information a menu of confidence levels, allowing a staffing administrator to select the confidence that the SSL is not exceeded for the next shift. For example, a menu including 50%, 75%, 90%, 95%, and 99% is presented to a user. When the staffing administrator selects 95%, a staffing level component produces a related Staffing Level (SL) parameter to be used in an SSL computing component within a time and attendance service 128. In an embodiment the SL is determined based on an assumption, a model or an estimate of the probability distribution function that relates SL to confidence level.

In an embodiment, when an incremented baseline staffing level is computed by time and attendance service 128 it is displayed on user interface 142 to nursing administrator. For example, a display message on user interface 142 informs a user that "staffing level for next shift is computed to be 14." In an embodiment the incremented baseline staffing level takes the form of a total staff level. In an embodiment an incremented baseline staffing level takes the form of an integer number of additional non-scheduled staff to be filled in the upcoming shift. In an embodiment a display message on user interface 142 informs the user that 2 additional non-scheduled nursing personnel will be needed for the upcoming shift, and a recommended action and a prompt are presented. A recommended action may include a staff request notification of on-call staff, a request notification to a temporary nursing agency, and a pull-request, that requests non-critical nursing staff to suspend ordinary duties and to assist a critical care unit. In an embodiment, a nursing staff administrator selects the option resulting in the recommended action being carried out. In an embodiment such requests are not presented to an administrator prior to execution, but a recommended action is instead automatically taken subject to predefined preferences, and a notification is presented on user interface 142 that the action was taken due to staffing forecast. In an embodiment, the number of additional staff requested is presented to a nursing staff administrator on user interface 142.

In an embodiment, an incremented baseline staffing level is computationally evaluated using one or more statistical process control (SPC) methods, such as $\bar{X} \pm 2SD$, cusum, and Shewhart-type multi-rule SPC. In an embodiment an SPC method sets one or more rules related to one or more metrics related to one or more limits above and/or below an average value. An SPC method uses these limits as process control limits, when these bounds are exceeded for a metric under certain conditions specified by a rule. For example, with a plus and minus two standard deviation limit, according to a first rule the appearance of two or more samples outside of this control region in a short period of time such as 5 samples indicates that the variance encountered has increased over that which had been historically experienced. As another exemplary rule, two samples within a count of 8 or fewer samples that are greater than 3 standard deviations away from the mean indicate increased variance. Further, a cumulative sum of a statistic may be maintained as a metric that approximates an estimate of a mean value of a parameter. When this cumulative sum deviates from prior estimates by a threshold amount above or below, this too may be used as metric used in accordance with a rule as an indication that variation of the process has increased. In an embodiment, an upper limit and a lower limit is selected as a multiplicative constant number of standard deviations above and/or below an average value, to define a control region.

One or more SPC rules, when satisfied, generate an alert to the process observer to inspect the process and to investigate for possible causes of increased variation. One or more rules may be used to prompt an indication to a user that the process is no longer in-control and stable. In an embodiment, a computer 120 such as a server computationally evaluates incremented baseline staffing level and/or one or more constituent parameters using an SPC method. When a predefined rule is evaluated and found to be true, server 120 running a time and attendance service at 128 sends a message to an administrator operating user interface 142 at a remote computer such as a mobile computer. In an embodiment, the message provides one or more actionable user interface elements as well as text such as "Alert-critical care nurse staffing algorithm as exceeded process control limits, click here for process details." In an embodiment, when selected, the actionable user interface element presents the demand variance estimate, the supply variance estimate, the safety-stock-over-leadtime value, and/or a time series and rule details that indicated the process is out of control, and/or unstable.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as a local or distributed stack in the cloud, on one or more personal computers or servers such as system 120, and/or a computing device running interface 142. In some embodiments, interface 142 operates in conjunction with software stack 125.

In embodiments, variables mapping (or indexing) service 122 and records/documents ETL service 124 provide services that facilitate retrieving frequent item sets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, these services may invoke software services 126.

Computation services 126 perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org); R-system modules or packages including for example, SCperf, forecast, or similar services. In an embodiment, computation services 126 include the services or routines, which may be embodied as one or more software agents or routines such as the example embodiments of computer program routines illustratively provided in FIG. 6. In some embodiments, software services 126 use EHR or clinical document services 128, which provide a framework for accessing and processing text corpuses such as unstructured clinical narratives of patient information. Services 128 may also include time and attendance services that may be used for managing staffing and patients. Some embodiments of stack 125 may further use Apache Hadoop and Hbase framework (not shown), or similar frameworks operable for providing a distributed file system, and which in some embodiments facilitate provide access to cloud-based services such as those provided by Cerner Healthe Intent®. Additionally, some embodiments of stack 125 may further comprise one or more services stream processing service(s) (not shown). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with EHR system 160, acuity system 165, and/or time/attendance system 163. Further, although depicted as a single storage data store, data store 121 may comprise one or more data stores, or may be in the cloud.

Figure 1B:
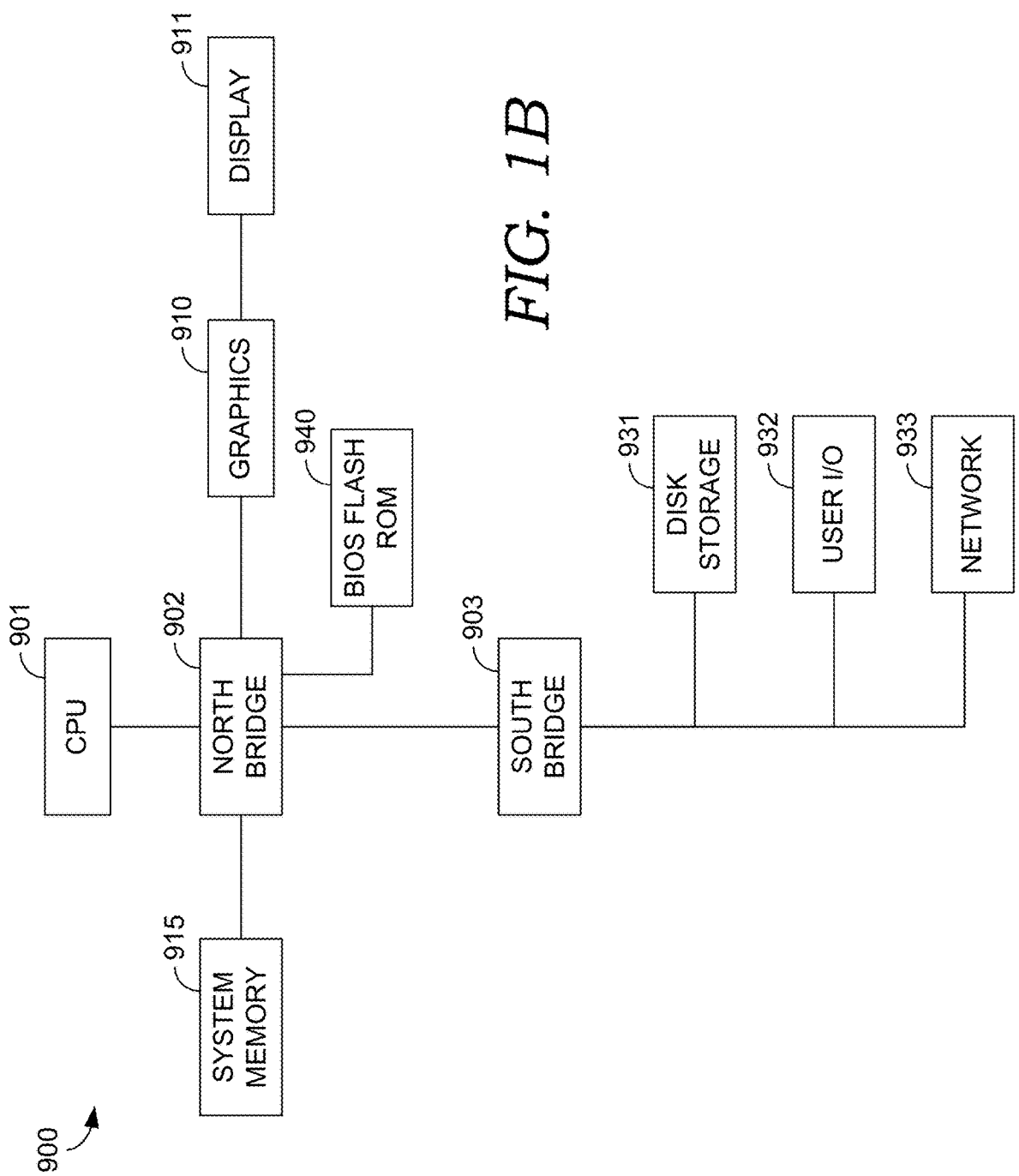

Turning briefly to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2:
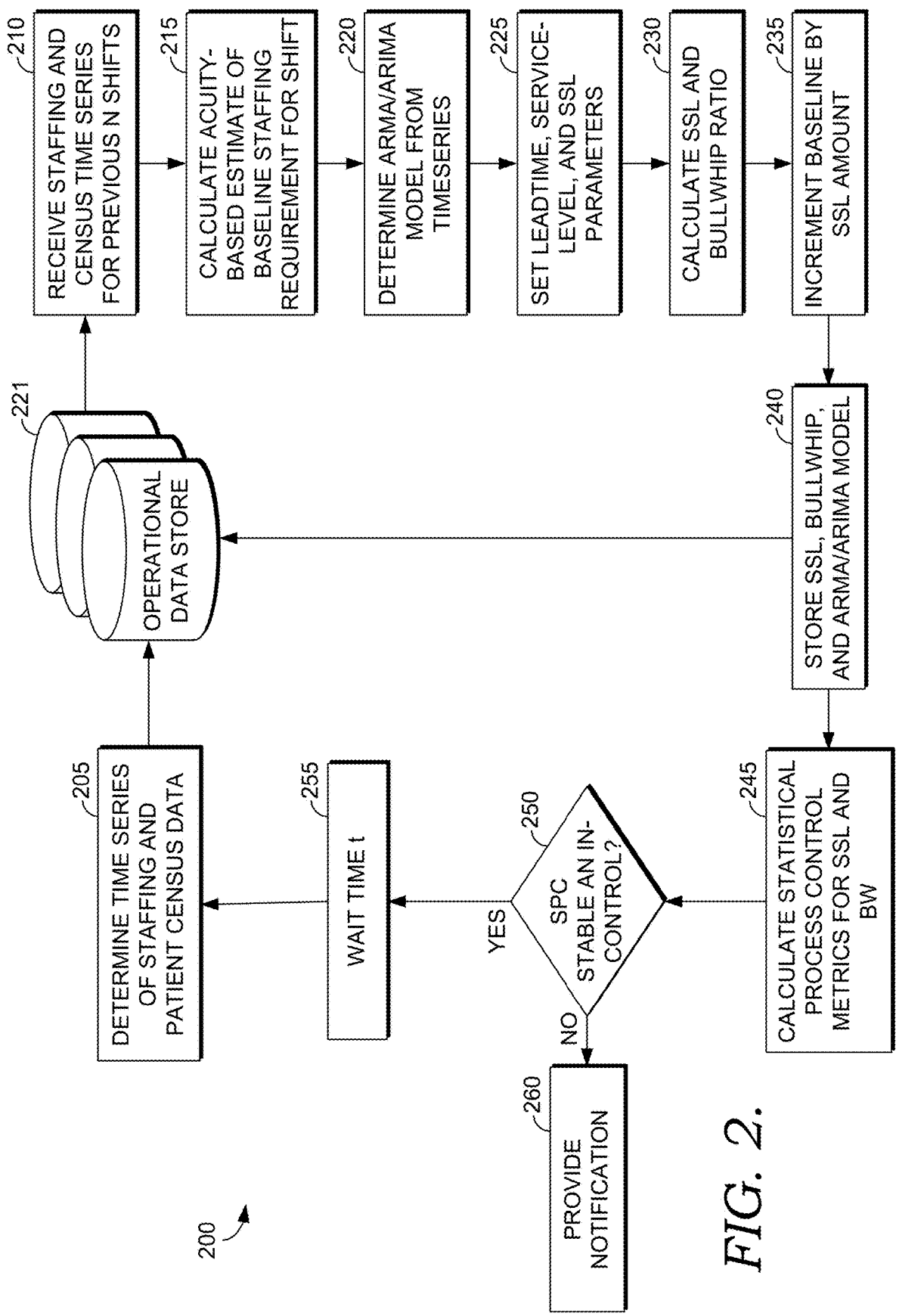
FIG. 2 depicts a flow diagram of a method for generating an SSL model based on demand for use in labor forecasting, in accordance with an embodiment of the invention.

Turning now to FIG. 2, an example embodiment is illustratively provided of a method 200 for generating an SSL model based on demand for use in health services nursing staff forecasting. At step 205, determine a time series of staffing and patient census data. In an embodiment, time series information may be determined from patient and staffing data as it becomes available, and may be stored in operational data store 221, which may be embodied as storage 121. At step 210, receive staffing and census time series for previous N shifts. In one embodiment, step 210 comprises receiving representative historical patient census data and nurse staffing data (e.g. previous 100 shifts for nursing unit X), and which may be received from EHR 160, patient acuity system 165, time/attendance system 163, or other record system (shown as operational data store 221).

At step 215 determine acuity-based forecast for upcoming shift(s) staffing requirements ("baseline"). In an embodiment, nurses within the present shift periodically perform an acuity assessment for each current patient within an acute care unit, e.g. by entering biological vitality measurement data into an applet on a tablet computer such as acuity system 165, which in turn processes the acuity data and stores the data within an operational data store 121. A baseline staffing requirement is computed at 215 taking into account one or more factors, including at least the acuity of one or more patients present in the acute care unit in the present shift. At 215 the acuity data is retrieved and processed to form a baseline staffing requirement that is based on this acuity. In an embodiment, at 215 the baseline staffing requirement is computed incorporating one or more equations and/or rules related to one or more factors in the acute care facility. In an embodiment the current patient census is a factor. For example, an acute care unit has a census of X patients in a newly arrived, post-operative state that must be monitored for particular complicating developments, a census of Y patients in an unknown condition requiring additional diagnostic procedures to determine acuteness, and a census of Z patients that are in a long-term recovery process that requires improvement and stabilization before surgery can be attempted. An embodiment that incorporates census weights the parameters X, Y and Z separately as to the number of nursing staff needed for each type of patient. Likewise an embodiment incorporates census when it simply has at least one nurse for each pair of patients estimates the number of nurses needed at approximately $(X+Y+Z)/2$. An embodiment that incorporates acuity sets a threshold of trauma score, and patients below that threshold trauma level are deemed to be high need, more likely to require invasive procedures, and so weighted with additional staff members. An embodiment incorporates the trend of trauma score to predict release of patients from the critical care unit, and thereby computes baseline staffing level to incorporate patient turnover. An embodiment computes baseline staff level using a schedule of planned intake of patients who are scheduled for surgery. In an embodiment a scheduled patient release is incorporated into a computed baseline staffing level. An embodiment of computing baseline staff level incorporates the time of day, the time of week, and the time of year which on certain occasions affects the expected patient turnover for that time-frame. For example, a weekend shift is expected to have low turn-over, because patients are unlikely to be released after stabilizing procedures, because many procedures will not be scheduled until the first working day of the new week. In an embodiment a number of life-sustaining procedures in the prior shift is incorporated into an estimated staffing level. For example, the number of life-sustaining procedures in the next shift is estimated to be the same as in the prior shift. In an embodiment the estimated staffing level incorporates the number of life-sustaining procedures that are planned in the next shift. In an embodiment the estimated staffing level incorporates a historical workload time series. For example, when nurses in the prior shift have been operating at more than 75% work load, this is taken as a sign for a rule that predicts that additional staff will likely be necessary in a succeeding shift. In an embodiment a historical staffing time series is used to form the present staffing level estimate. For example, on a holiday week-end historically there are historically fewer staff members available for on-call status, and/or more likely to be staff no-shows, hence additional staff is incorporated into the baseline staffing level to insure no shortfall.

At step 220, one or more model parameters are determined from a census time series. In an embodiment, at 220 model parameters are determined according to an autoregressive moving average (ARMA)/autoregressive integrated moving average (ARIMA) model. In an embodiment model parameters include a vector of one or more autoregressive parameters, and/or one or more moving average weights, which may be collectively referred to as a vector φ, and are estimated from the historical timeseries. In some embodiments, step 220 may further comprise determining a modeling method for SSL (for example, minimum mean-square error [MMSE], simple moving average [SMA], or exponential smoothing [ES]). In an embodiment, the model method is selected based on a ranked goodness-of-fit test performed for each candidate model upon the historical time series. The best-fit model is selected as the model to be used by the method.

At step 225, parameters are set for SSL modeling. Parameters set may include for example, non-zero leadtime L; a for ES method; order p for SMA method; and/or service-level SL. In an embodiment a refers to a parameter for an employed exponential smoothing algorithm used in the computation of SSL. In an embodiment a is chosen to be 0.7. In an embodiment a is chosen to be in a wider range of smoothing, between 0.5 and 0.999. In an embodiment a Time and Attendance service component 128 receives a lead-time-value component from a user interface 142 through direct entry or direct selection. In an embodiment an SSL computing component within a Time and Attendance service component 128 receives a lead-time-value from storage 121. In an embodiment storage 121 had received the lead-time-value which was computed by a lead-time-value estimation component, or had defined lead-time-value within a service setup file or had stored an administrator selection or entry.

At step 230, calculate the current SSL. In an embodiment the SSL is computed using an exponential smoothing calculation based on the parameters of an autoregressive model of the census time series. In an embodiment, the SSL is computed based on one or more libraries of the R system such as the forecast and SCperf libraries. In an embodiment the calculation of SSL depends upon a recent window of shift data such as the last 30 shifts. In an embodiment SSL is determined based on an input non-zero leadtime. In an embodiment, the SSL is computed based on estimated model parameters such as one or more of lead time, model order, service level, and one or more autoregressive parameters.

At 230 a bullwhip ratio is computed. In an embodiment, the bullwhip ratio is computed from a model of the staffing demand process incorporating one or more of exponential smoothing, one or more autoregressive parameters, lead time, model order, and service level. In an embodiment bullwhip ratio is computed based on an input non-zero leadtime.

At step 235, the baseline staffing is incremented by SSL value to determine staffing that will achieve compliance per the service level parameter. In some embodiments, at step 240, the SSL, bullwhip ratio, and ARMA/ARIMA models may be stored. In an embodiment, at 235, after computation of the staffing level for a next shift that is incremented by SSL, a notification may be provided, such as an alert issued to a manager. In an embodiment, one or more employees are notified of changes in staffing scheduling (for example, calling in additional employees or notifying the employees that they are not needed for a particular shift). Additionally, in one embodiment at 235 automatic scheduling or altering of the schedule of staffing is performed based on the staffing level that is incremented by SSL.

At step 245, one or more statistical process control (SPC) metrics are calculated. In an embodiment an SPC metric is calculated evaluating SSL. In an embodiment an SPC metric is calculated based on bullwhip ratio. In an embodiment, SSL and bullwhip ratio are analyzed jointly using a multivariate SPC method. In one embodiment, step 245 comprises, comparing current SSL and bullwhip ratio to recent historical values for nursing unit using, for example, Hotelling T2 multivariate statistical process control ("SPC"). At 250 a decision is made based on one or more calculated metrics whether or not the statistical process is a stable in-control process. At step 250, if the SPC is stable and in control, then method 200 proceeds to step 255. If the SPC indicates instability, such as an emerging statistically significant shift, drift, or change in variance, then at step 260 a notification may be provided, such as an alert issued to a manager. In one embodiment, step 260 comprises notifying employee(s) of changes in staffing scheduling (for example, calling in additional employees or notifying the employees that they are not needed for a particular shift). Additionally, in one embodiment, step 260 comprises automatically scheduling or altering the schedule of staffing based on the model. At step 255, where the SPC is stable and in control, then method 200 waits a time t, such as 1 to 12 hours, before returning to step 205, where a timeseries is determined (which may comprise updating a previously determined timeseries).

Figure 3:
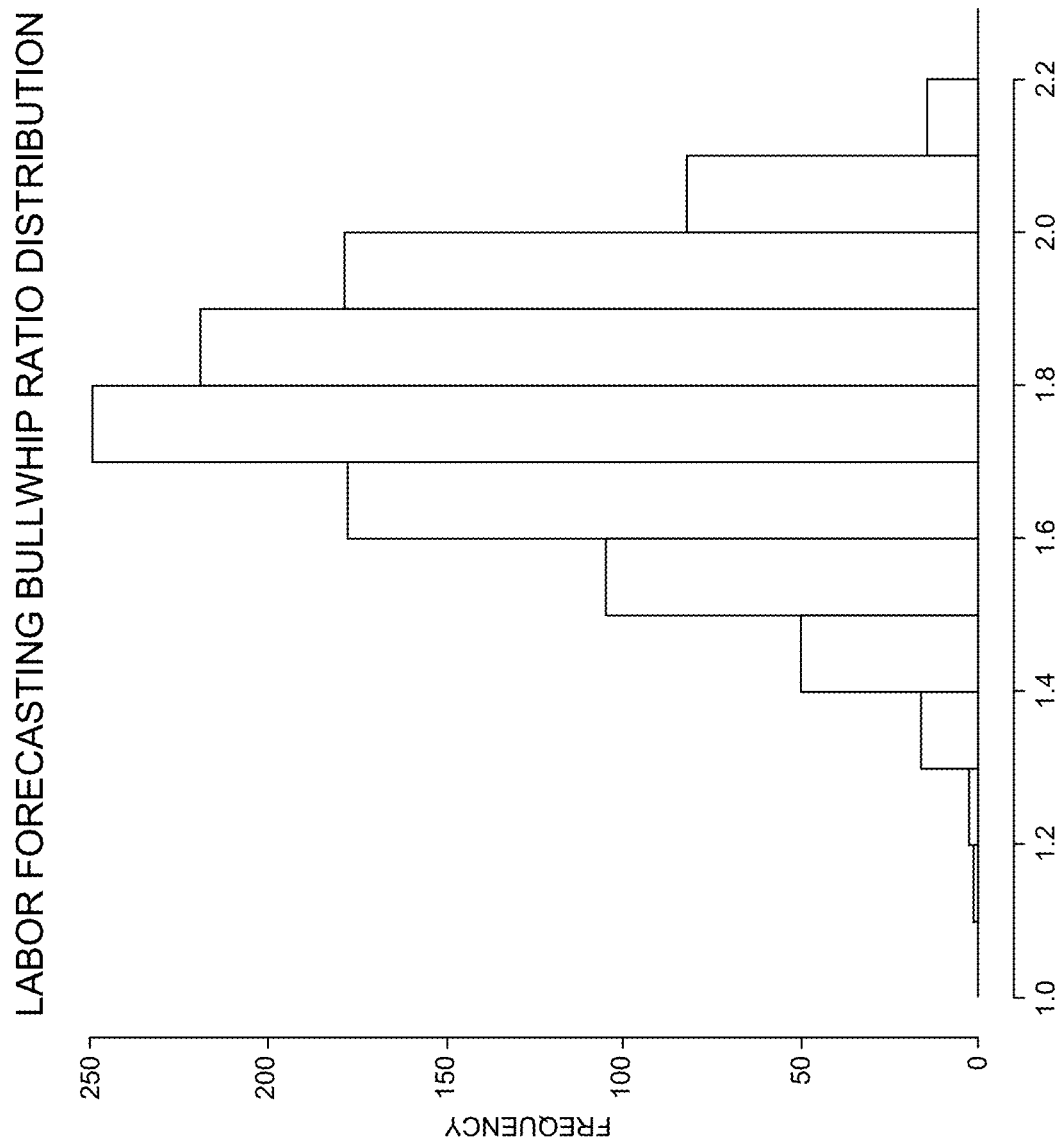
FIG. 3 depicts a bullwhip distribution determined from nurse staffing data, in accordance with an embodiment of the invention.
Figure 5:
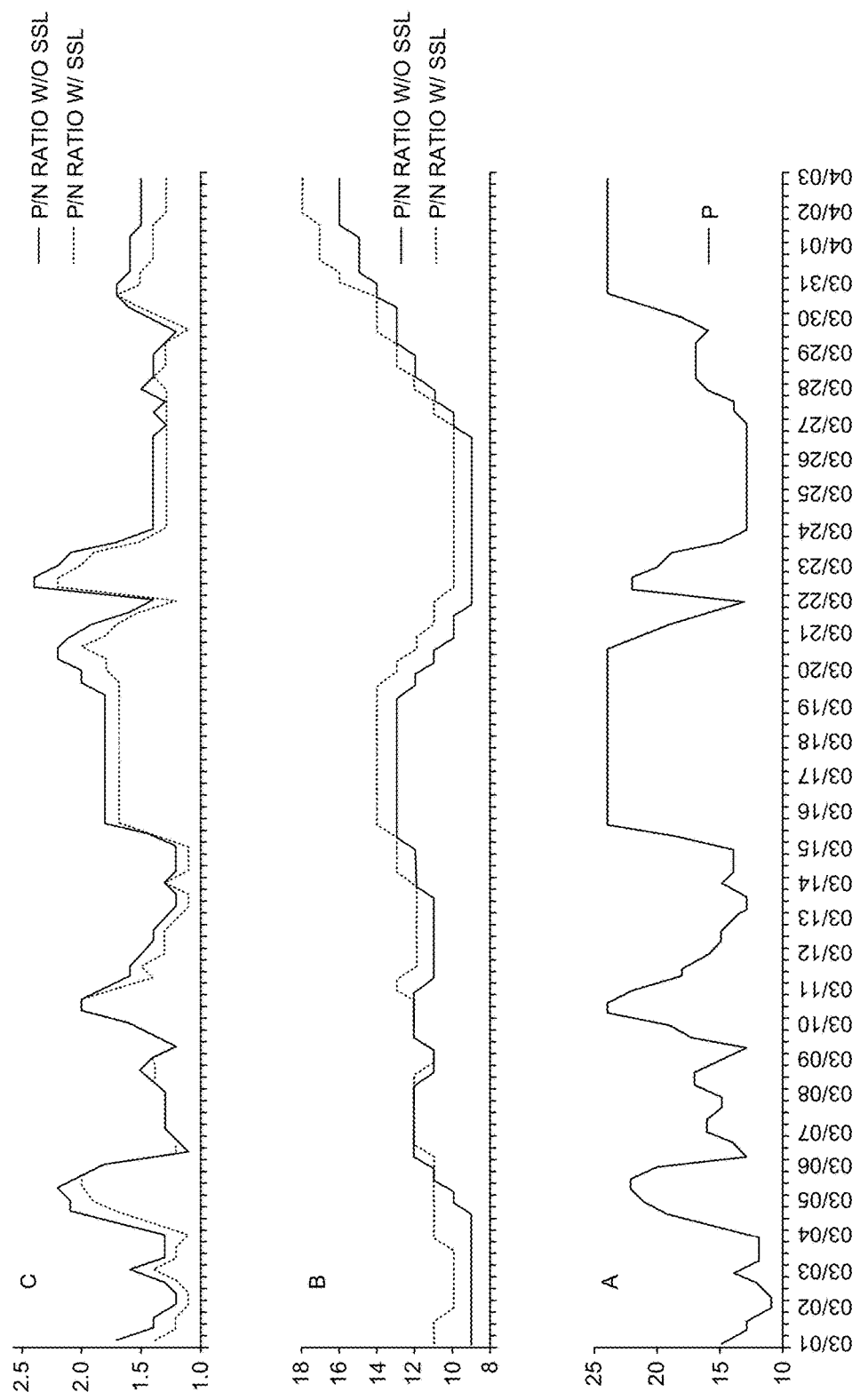
FIG. 5 depicts example 30-day segment for patient census and nurse staffing with and without SSL, in accordance with an embodiment of the invention.

With reference to FIGS. 3-5, an example is provided of one embodiment of the invention reduced to practice using service levels (SL) of 95%, meaning that the models were required to predict SSL staffing levels such that exceedance of the P/N=2.00 limit would occur no more frequently than 5% of the time. This example embodiment was reduced to practice using a computer running the Linux operating system, the open-source statistical software package R and the R packages forecast and SCperf, such as described in connection to FIGS. 1A and 1B. In this regard, a cloud-based computing configuration is one alternative embodiment of the invention. Alternatively, a stand-alone server or other computing device equipped with suitable connectivity to the records systems by which the time series are acquired may likewise be utilized in another embodiment.

For this example embodiment, an illustrative series was received, consisting of de-identified, privacy-protected, secondary-use-permitted HIPAA-compliant records for medical intensive care units (1 Mar. 2012 to 28 Feb. 2013). We performed a multicenter longitudinal study in two 24-bed adult medical ICUs located in two U.S. university hospitals. De-identified, HIPAA-compliant, privacy-protected data were extracted from observational data warehouses maintained by Cerner Corporation under data-rights agreements provided by participating institutions for secondary use of the de-identified information. Information pertaining to every patient admitted to these ICUs between Mar. 1, 2012, and Feb. 28, 2013, was used in the modeling analyses. Cerner Health Facts® data warehouse contained complete flowsheet, laboratory, pharmacy, procedures, diagnoses, and other electronic health record (EHR) information, each date-time stamped as to their occurrence times. Caregiver presence at work was recorded on an hourly basis, and other data were as extracted from the nursing time and attendance software systems, as shown in the table of FIG. 4.

In order to provide a numerically reliable characterization of the demand and response processes in critical care units, initial results of the example embodiment operated on a time series of at least a minimum number of shifts (for example data from 100 shifts). Autoregressive-moving average (ARMA) models of first- and second-order were evaluated, with and without provision for seasonality, and with and without provision for linear drift in demand 20-21 AR(1), AR(1,1), and AR(1,0,1) models produced acceptable fits to the staffing time series data. Minimum Mean Square Error (MMSE), Simple Moving Average (SMA) and Exponential Smoothing (ES) methods were evaluated. Preliminary results suggest that exponential smoothing with an alpha smoothing coefficient of approximately 0.7 performs in a consistent manner that is stable over the span of 1 year.

With reference to FIGS. 3 and 4, a significant bullwhip effect (ratio of the unconditional variance of the nurse staffing response process to variance of the patient demand process>1.00) was determined in the staffing data for each of the units studied. The unit implementing demand forecasting with an SSL regime and a target 95% service level had a modestly lower bullwhip ratio (1.42 (0.24) compared to 1.55 (0.27), p<0.001) and achieved a 2.0 P/N exceedance rate of only 2.0% whereas the comparator unit exceeded the 2.0 P/N ratio on 10.1% of the shifts, as shown in the table of FIG. 4. The SSL increment of nursing resources above what was recommended by routine acuity-based forecasting software averaged 0.96 nurses above the customary forecast, an increase of 8.4%. While not insubstantial, this incremental workforce spending needed to assure compliance with the state nurse staffing regulations was far smaller than had been anticipated for the 2.0 P/N limit.

With reference now to FIG. 5, a plot of a typical 30-day segment is shown for patient census ("P") and nurse staffing ("N") in one of the units. In this example embodiment, the acuity-based forecasting process recommended staffing levels shown in solid line ("N w/o SSL"), and the safety-stock-over-leadtime recommended staffing levels are shown in dotted line ("N w/SSL"). Patient-to-nurse ratio is reflected in the bottom chart of FIG. 5. It is observed that during periods where patient census rapidly rises to unit capacity (for example, 03/15 and 03/30), the SSL model responds quickly with staff increments that reflect the historical ARMA properties of the demand and response processes that are incident upon the unit, from which the model's time-dependent SSL level predictions are derived. Similarly, during intervals when fluctuations in demand and in labor response are less pronounced (for example, 03/06 to 03/09), the SSL model yields recommendations that are very nearly the same as routine acuity-based forecasts or lag only about one shift behind the acuity-based forecast.

Studies have established a clear relationship between P/N ratio>2.00 and increased ICU mortality. It is this relation between nursing resources and patient outcomes that have motivated regulatory initiatives to set nurse staffing standards. However, the prevalence of ICU shifts with P/N ratio>2.00 remains high, and conventional wisdom holds that provisioning staff levels to comply with the standards will necessarily result in financial losses for institutions or be impractical to implement for other reasons. By contrast, embodiments indicate that ICU patient demand and nurse staffing response processes may be readily, effectively modeled by ARMA or ARIMA methods so long as sufficient data (for example, in one embodiment data for 100 or more consecutive shifts) are available, and the properties of the resulting ARMA or ARIMA models can be applied using safety-stock-over-leadtime models. Moreover, some embodiments create predictive models that take into account non-zero and stochastically varying leadtime for sourcing nurses to work ICU shifts and avoid deficits or 'stock-outs' of nurses in units facing wide fluctuations in census and acuity and patient turnover.

In embodiment 1, a computer-readable media having computer-executable instructions embodied thereon that when executed, facilitate a method for acuity-based forecasting of staffing requirements comprises augmenting baseline staffing requirements for one or more future shifts by a variable amount that is termed a safety-stock to prevent shortages in the presence of variable demand and to do so within a determined service level and with a non-zero leadtime for provisioning labor resources to work said future shift(s).

Embodiment 2 comprises the media of embodiment 1, wherein the forecast shifts' baseline staffing requirements are calculated using patient acuity measures, patient census, patient turnover and scheduled intake and departures, number of life-sustaining procedures per shift or per other time unit, historical workload time series, or other metrics as are known to those practiced in the art.

Embodiment 3 comprises the media of embodiment 1, wherein the method comprises using mathematical modeling that includes autoregressive (AR), autoregressive moving average (ARMA), autoregressive integrated moving average (ARIMA), or other forecasting methods applied to historical time series for the venue in which said forecasts are to be produced.

Embodiment 4 comprises the media of embodiment 3, wherein process parameters determined by AR, ARMA, or ARIMA modeling are used as inputs for determining safety-stock-over-leadtime (SSL) estimates by analytical formula or by Markov Chain Monte Carlo simulation, as known to those practiced in the art of supply chain management.

Embodiment 5 comprises the media of embodiment 1, wherein the non-zero lead time for sourcing labor is constant.

Embodiment 6 comprises the media of embodiment 1, wherein the non-zero lead time for sourcing labor is optionally time-varying and either stochastic or varying according to a deterministic analytical formula such as linear or exponentially-weighted moving average.

Embodiment 7 comprises the media of embodiment 3, wherein the modeling may incorporate provisions for time-dependent shifts, linear drift trends, or seasonal cyclical effects.

Embodiment 8 comprises the media of embodiment 1, wherein the method includes ARMA/ARIMA forecasting from historical time series, determination of SSL, and determination of bullwhip ratio.

Embodiment 9 comprises the media of embodiment 1, wherein the forecasting and SSL estimation processes are repeated with a frequency commensurate with frequency of shift changes, in cases where time-and-attendance and assignments data are maintained with shift-wise time-resolution.

Embodiment 10 comprises the media of embodiment 1, wherein the forecasting and SSL estimation processes are optionally repeated with a greater-than-shift-wise frequency in cases where fractional-shift staffing is contemplated and time-and-attendance and assignments data are available with higher time precision, preferably hourly.

Embodiment 11 comprises the media of embodiment 1, wherein said SSL estimates are combined with acuity-based forecasts to yield a net staffing recommendation incorporating the safety-stock-over-leadtime labor increment over the baseline recommendation.

Embodiment 12 comprises the media of embodiment 1 wherein the forecasting staffing requirements is based on determining a 'bullwhip ratio', defined as the ratio of the unconditional variance of the labor-provisioning response process to the unconditional variance of the demand process.

Embodiment 13 comprises the media of embodiment 12, wherein each consecutive determination of the bullwhip ratio is stored in computer readable media.

Embodiment 14 comprises the computer readable storage medium of embodiment 13, wherein a plurality of SSL values are assembled in a time series and a plurality bullwhip ratio values are assembled in a second time series.

Embodiment 15 comprises the computer readable storage medium of embodiment 14, wherein said time series are analyzed using statistical process control methods, such as $\overline{X} \pm 2SD$, cusum, or Shewhart-type multi-rule SPC.

Embodiment 16 comprises the computer readable storage medium of embodiment 15, wherein the SSL and bullwhip ratio are analyzed jointly using multi-variate statistical process control methods, such as Hotelling T2 SPC.

Embodiment 17 comprises the computer readable storage medium of embodiment 16, wherein transgressions of SPC control levels cause the computer program to emit a warning notification to managerial or supervisory personnel responsible for determining staffing levels.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A computer-performed method for forecasting staffing level of a staffing position in an acute care facility comprising:
   computing, on a computer system, a baseline staffing level for a next shift based on patient acuity assessments made in a prior shift; and
   incrementing the baseline staffing level by a Safety-Stock-over-Leadtime (SSL), wherein the SSL is computed using an improved estimation process comprising:
   receiving a census time series,
   determining one or more model parameters that are derived from the census time series,
   receiving a lead-time-value, and
   computing the SSL, using an auto-compute option on the computer system, at a time that allows a lead-time to expire in the computer system before the next shift, using the lead-time-value and the one or more determined model parameters comprising at least one of a vector of one or more autoregressive parameters and one or more moving average weights, based on the census time series;
   displaying the incremented baseline staffing level on a computer display device; and
   computationally evaluating the incremented baseline staffing level using one or more statistical process control methods, wherein computationally evaluating comprises calculating statistical process control metrics for one or more process parameters and determining whether the statistical process is a stable in-control process,
   based on determining the statistical process is a stable in-control process, generating an updated schedule of staffing resources based on the incremented baseline staffing level, and communicating to at least one of the staffing resources an indication of the updated schedule.

2. The method of claim 1, wherein the one or more process parameters comprises SSL.

3. The method of claim 1, further comprising providing a notification message to a staffing supervising user when the method has determined that the statistical process is not a stable in-control process.

4. The method of claim 1, wherein the one or more model parameters comprises one or more of a set of autoregressive coefficients, and a set of moving average coefficients.

5. The method of claim 1, wherein the computing the SSL comprises using an exponential smoothing of factor alpha.

6. The method of claim 5, wherein alpha is chosen in a range between 0.5 and 0.999.

7. The method of claim 1, wherein a service level is predetermined by a related confidence level that estimates a probability that a demand level will not exceed the computed SSL.

8. The method of claim 1, wherein the method for forecasting staffing level further comprises storing the lead-time-value as a constant to be used as a lead-time employed for one or more shifts in a pattern of shifts within a day.

9. A computerized device for forecasting staffing level of a staffing position in an acute care facility comprising:
   one or more processors, and
   computer storage memory having computer-executable instructions stored thereon which, when executed by the one or more processors, implement a method of forecasting staffing level of a staffing position in an acute care facility comprising:
   computing, on the computerized device, a baseline staffing level for a next shift based on patient acuity assessments made in a prior shift; and
   incrementing the baseline staffing level by a Safety-Stock-over-Leadtime (SSL), wherein the SSL is computed using an improved estimation process comprising:
   receiving a census time series,
   determining one or more model parameters that are derived from the census time series, comprising at least one of a vector of one or more autoregressive parameters and one or more moving average weights, based on the census time series
   receiving a lead-time-value,
   computing the SSL, using an auto-compute option on the computerized device, at a time that allows a lead-time to expire in the computerized device before the next shift,
   using the lead-time-value, and the one or more determined model parameters,
   computationally evaluating the incremented baseline staffing level using one or more statistical process control (SPC) methods chosen from the set consisting of $\overline{X} \pm 2SD$, cusum, and Shewhart-type multi-rule SPC,
   calculating statistical process control metrics for a bullwhip ratio formed by computing a variance of staffing demand level, computing a variance of staffing supply level, forming a bullwhip ratio comprising a variance parameter of staffing supply level in a numerator and a variance parameter of staffing demand level in a denominator, and calculating statistical process control metrics for SSL, and analyzing statistical process control metrics jointly using a multi-variate statistical process control method,
   determining the bullwhip ratio is above a threshold, and based on determining the bullwhip ratio is above a threshold,
   generating an updated schedule of staffing resources based on the incremented baseline staffing level, and communicating to at least one of the staffing resources an indication of the updated schedule; and
   a display that presents the incremented baseline staffing level and the updated schedule of staffing resources on a computer display device for a computer user.

10. The computerized device of claim 9, wherein the forecasting of staffing level further comprises storing the lead-time-value as a constant to be used as a lead-time employed for one or more shifts in a pattern of shifts within a day.

11. The computerized device of claim 9, wherein the forecasting of staffing level further comprises estimating the lead-time-value in a lead-time estimation component prior to the receiving of the lead-time-value.

12. The computerized device of claim 11, wherein the lead-time estimation component uses one or more of a linear estimate, an exponentially-weighted moving average, a computation at a plurality of times within a shift, a computation once each shift change, and a computation with data isolated for similar shifts within a daily cycle.

13. The computerized device of claim 9, wherein the computing of a baseline staffing level for a next shift comprises using one or more of an element chosen from a set consisting of: a patient acuity measure, a patient census, a patient turnover, a schedule of intake and departure, a number of life-sustaining procedures in the prior shift, a number of life-sustaining procedures planned in the next shift, a historical workload time series, and a historical staffing time series.

14. The computerized device of claim 9, wherein forecasting of staffing level further comprises providing a notification message to a staffing supervising user when the method has determined, based on computationally evaluating the incremented baseline staffing level, that the statistical process is a stable in-control process.

15. A computer-performed method for forecasting staffing level of a staffing position in an acute care facility comprising:
    computing, on a computer system, a baseline staffing level for a next shift based on patient acuity assessments made in a prior shift; and
    calculating a current Safety-Stock-over-Leadtime (SSL), using an auto-compute option on the computer system, at a time that allows a lead-time to expire in the computer system before the next shift, using an exponential smoothing calculation based on an autoregressive model of the census time series and a recent window of shift data based on an input non-zero lead-time;
    incrementing the baseline staffing level by the current SSL;
    generating an updated schedule of staffing resources based on the incremented baseline staffing level, and communicating to at least one of the staffing resources an indication of the updated schedule; and
    displaying the incremented baseline staffing level on a computer display device.

* * * * *

UNITED STATES PATENT AND TRADEMARK OFFICE
CERTIFICATE OF CORRECTION

PATENT NO. : 11,062,802 B1
APPLICATION NO. : 15/173063
DATED : July 13, 2021
INVENTOR(S) : Douglas S. McNair It is certified that error appears in the above-identified patent and that said Letters Patent is hereby corrected as shown below:

In the Drawings

Sheet 5 of 7, Figure 4, Line 1, delete "LEVEL" and insert -- LEVEL) --.

In the Specification

Column 2, Line 14, delete "invention" and insert -- invention; --.

Column 4, Line 46, delete "rubust" and insert -- robust --.

Column 5, Line 5, delete "manner" and insert -- manner. --.

Column 10, Line 27, delete "Healthe Intent®" and insert -- HealtheIntent® --.

Column 12, Line 64, delete "a" and insert -- α --.

Column 12, Line 66, delete "a refers" and insert -- α refers --.

Column 13, Line 1, delete "a" and insert -- α --.

Column 13, Line 2, delete "a is" and insert -- α is --.

In the Claims

Column 18, Line 7, in Claim 8, delete "a lead-time" and insert -- the lead-time --.

Signed and Sealed this
Third Day of October, 2023

*Katherine Kelly Vidal*

Katherine Kelly Vidal
*Director of the United States Patent and Trademark Office*